(12) United States Patent
Zhu

(10) Patent No.: US 6,264,610 B1
(45) Date of Patent: Jul. 24, 2001

(54) COMBINED ULTRASOUND AND NEAR INFRARED DIFFUSED LIGHT IMAGING SYSTEM

(75) Inventor: Quing Zhu, Mansfield Center, CT (US)

(73) Assignee: The University of Connecticut, Storrs, CT (US)

( * ) Notice: Subject to any disclaimer, the term of this patent is extended or adjusted under 35 U.S.C. 154(b) by 0 days.

(21) Appl. No.: 09/565,508

(22) Filed: May 5, 2000

Related U.S. Application Data (60) Provisional application No. 60/132,547, filed on May 5, 1999.

(51) Int. Cl.[7] .................................................. A61B 8/00
(52) U.S. Cl. ............................................................ 600/443
(58) Field of Search ................................. 600/437, 407, 600/443, 447, 448, 438

(56) References Cited

U.S. PATENT DOCUMENTS 5,713,356 * 2/1998 Kruger .................................. 600/443
5,999,836 * 12/1999 Nelson et al. ........................ 600/407

* cited by examiner

Primary Examiner—Marvin M. Lateef
Assistant Examiner—Maulin Patel
(74) Attorney, Agent, or Firm—Cantor Colburn LLP

(57) ABSTRACT

A combined ultrasound and near infrared (NIR) diffused light imaging system includes a combined ultrasound and NIR light probe operatively connected to an ultrasound imaging system and an NIR diffused light imaging system. The combined ultrasound and NIR light probe comprises ultrasound transducer elements distributed in a rectangular matrix. Each element works in pulse-echo mode to provide spatial images of tissue at various depths. The optical system includes laser diode light sources and photomultiplier tube detectors. Measurement can be done at multiple source-detector positions to develop image-reconstruction schemes to determine absorption and scattering coefficients as well as oxygen and blood concentration of the tissue volume at various slice depths. A display device provides co-registration of acoustic and optical images output by the ultrasound and NIR diffused light imaging systems.

18 Claims, 5 Drawing Sheets

COMBINED ULTRASOUND AND NEAR INFRARED DIFFUSED LIGHT IMAGING SYSTEM

CROSS-REFERENCE TO RELATED APPLICATIONS

This application claims the benefit of U.S. Provisional Application No. 60/132,547, filed May 5, 1999, which is incorporated by reference herein.

BACKGROUND OF THE INVENTION

This invention relates primarily to the field of imaging and, more specifically, to an apparatus for the combined use of ultrasound and near infrared diffused light imaging.

Ultrasound imaging is a well-developed medical diagnostic that is used extensively for differentiation of cysts from solid lesions in breast examinations, and it is routinely used in conjunction with mammography to differentiate simple cysts from solid lesions. Ultrasound can detect breast lesions that are a few millimeters in size; however, its specificity in breast cancer detection is not high as a result of the overlapping characteristics of benign and malignant lesions. The sonography appearance of benign and malignant lesions have considerable overlapping features, which has prompted many radiologists to recommend biopsies on most solid nodules. Thus, the insufficient specificity provided by ultrasound results in a large number of biopsies yielding benign breast masses or benign breast tissue (currently 70 to 80 percent of biopsies yield benign changes).

Recently, optical diagnostics, based on diffusing near infrared (NIR) light, have been employed in breast cancer detection. Functional imaging with NIR light is made possible in a spectrum window that exists within tissues in the 700–900 nm NIR region, in which photon transport is dominated by scattering rather than absorption. Functional imaging with NIR light offers several tissue parameters to differentiate tumors from normal breast tissue. For example, functional imaging with NIR light has the potential to differentiate tumors from normal breast tissue through determination of blood volume, blood $O_2$ saturation, tissue light scattering, water concentration, and the concentration and lifetime of exogenous contrast agents.

While NIR imaging has the potential to improve tumor specificity, its relatively low resolution makes it unsuitable for morphological diagnosis. Its resolution is intrinsically limited by the diffusive nature of NIR light in tissue. Currently, typical NIR imaging instruments can distinguish simple structures approximately 1 centimeter in size; however, sharp edges are typically blurred by a few millimeters. Unfortunately, the relatively poor resolution of the optical reconstruction makes it difficult to take full advantage of the improved tumor specificity that would otherwise be provided by NIR imaging.

BRIEF DESCRIPTION OF THE INVENTION

The present invention relates to a novel design of a hybrid imaging probe consisting of a two-dimensional ultrasound array and near infrared light sources and detectors. The hybrid probe enables co-registration of ultrasound and near infrared diffusive light images of the tissue volume underneath the probe. Co-registered images provide high spatial resolution which is inherited from ultrasound imaging and high contrast from near infrared imaging. Co-registered images allow joint evaluation of tissue acoustic and optical parameters which will lead to the improved detection and diagnosis of cancers.

A combined ultrasound and diffused light probe for use in imaging of a medium includes a plurality of piezoelectric elements configured in a two-dimensional matrix (2-D array) to transmit ultrasound waves to the medium. The plurality of piezoelectric elements are also configured to receive ultrasound echoes from targets in the medium and to transform the ultrasound echoes into electrical signals. The probe further includes a near-infrared light source fiber and a near-infrared light detector fiber arranged proximate to the plurality of piezoelectric elements. The source and detector fibers are coupled to a light source and detector mounted on a near infrared system. The near-infrared light source is configured to project photon diffusion waves into the medium, and the near-infrared light detector is configured to detect reflected photon diffusion waves from targets in the medium.

In one embodiment, the plurality of piezoelectric elements are coupled to an ultrasound imaging system and the near-infrared light source and near-infrared light detector are coupled to a near-infrared imaging system. Because of the co-axial arrangement of the 2-D ultrasound array and near-infrared sensors, the ultrasound and near-infrared light images of the medium are co-registered. Therefore, an output display can be arranged to display the outputs or images of both systems with the same dimensions.

DETAILED DESCRIPTION OF THE INVENTION

Figure 1:
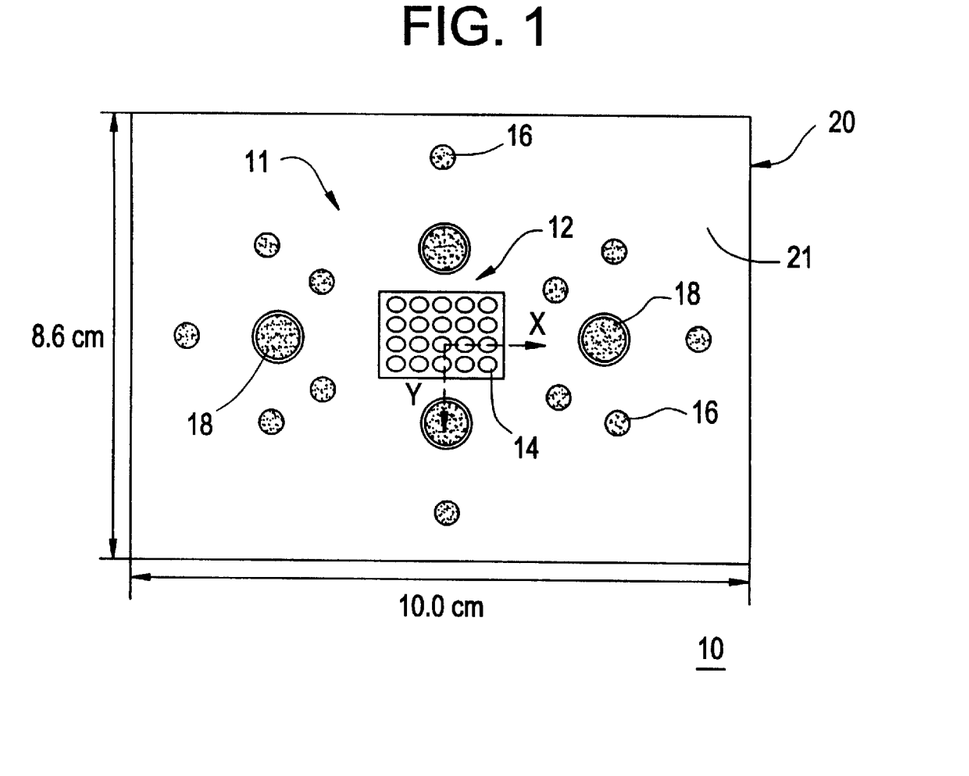
FIG. 1 is a combined ultrasound and NIR light probe of the present invention.

FIG. 1 shows the front face of a combined ultrasound and NIR light probe 10 of the present invention. The combined probe 10 consists of a two-dimensional (2-D) ultrasound array 12 comprising multiple ultrasound transducer elements 14 and an NIR optical array 11 comprising laser diode sources 16 and light detectors 18. The ultrasound array 12 and NIR sources 16 and detectors 18 are coaxially mounted on a common probe support 20. The ultrasound array 12 is located at the center of the combined probe 10 and NIR sources 16 and detectors 18 are distributed at the periphery of the ultrasound array 12. Preferably, combined probe 10 is sized to be hand-held. In this embodiment, the probe support 20 is made of a 10 cm by 8.6 cm plastic plate with a thickness of approximately 0.8 cm. The probe support 20 has a substantially flat face surface 21, which is directed towards the patient or target of interest.

The ultrasound array 12 is made of twenty ultrasound transducer elements 14, which may include small (approximately 1.5 mm in diameter) piezoelectric (PZT)

wideband crystals. Elements 14 extend through support 20 and are substantially flush with face surface 21 such that elements 14 project ultrasound waves outward from face surface 21. The elements 14 are distributed in a rectangular matrix located at the center portion of the probe 10, and the NIR sources 16 and detectors 18 are distributed around the rectangular matrix of elements 12. With the ultrasound array elements 14 deployed at the center portion, the array 12 can provide coherent images of the tissue volume underneath the probe 10. The ultrasound field of view depends on the steering capability of the array 12 and is, in general, larger than the geometric extension of the array 12.

Each ultrasound element 14 works in pulse-echo mode; i.e., it transmits and receives ultrasound pulses. In one embodiment, the central frequency of each element 14 is 5 MHz and the bandwidth is approximately 50%. The diameter of each element 14 is 1.5 mm and the outer diameter including the shell, which is disposed around the diameter of each element, is 2.5 mm. The elements 14 may comprise, for example, model number KS6-5-X as manufactured by Ultra Lab, Inc. The elements 14 are unfocused, so their angular responses are wide. The wide angular response permits formation of coherent beams from a group of the elements 14, called a subarray. The 3 dB beamwidth of each element 14 is approximately $\lambda/d$. Thus, at a wavelength ($\lambda$) of 0.3 mm and a diameter (d) of 1.5 mm, each element 14 has a transmitted beam that forms an 11.5 degree cone. The elements 14 are spaced by 4 mm in both x and y directions. The spacing represents a compromise between optimum field of view and resolution. With the array configuration shown in FIG. 1, the beams of neighboring elements 14 overlap and they are used to form the transmitted and received beams.

In the NIR optical array 11, twelve sources 16 and four detectors 18 are shown. Sources 16 are formed from optical fibers (source fibers) connected to a laser diode source (not shown). Each detector 18 is formed from an optical fiber (detection fiber) connected to a light detector (not shown). The source fibers and detector fibers extend through support 20, with the ends of each fiber being substantially flush with face surface 21. The source fibers and detector fibers are located generally at the periphery of the probe 10. It will be recognized by one skilled in the art, that sources 16 may include laser diode sources connected directly to probe 10, without the source fibers. Similarly, detectors 18 may include light detectors directly connected to probe, without the detector fibers.

Figure 2:
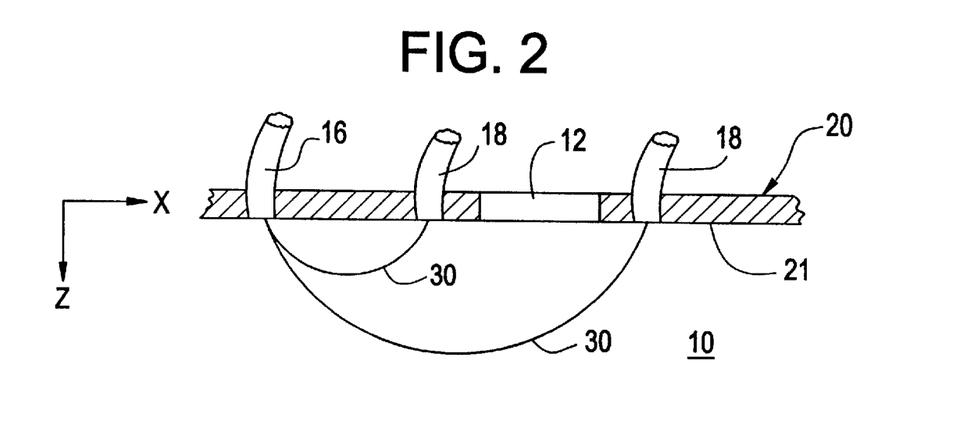
FIG. 2 is a two dimensional side view of photon diffusion paths between a source and two different detectors located at different distances from the source.

With the source-detector arrangement shown, the probability distribution of a photon path between any source 16 and detector 18 is banana shaped. FIG. 2 is a cross-sectional view of combined probe 10, providing a two-dimensional side view of photon diffusion paths 30 between a source 16 and two different detectors 18 located at different distances from the source 16. As a result of this distribution path, measurements made at all possible combinations of source-detector pairs at the periphery of probe 10 can be used to image the tissue volume underneath the probe 10, even though there are no NIR sources 16 or detectors 18 in the center position of the probe 10 (i.e. in the location of ultrasound array 12). Thus, the arrangement of sources 16 and detectors 18 allows the ultrasound array 12 to be located at the center position.

Figure 3:
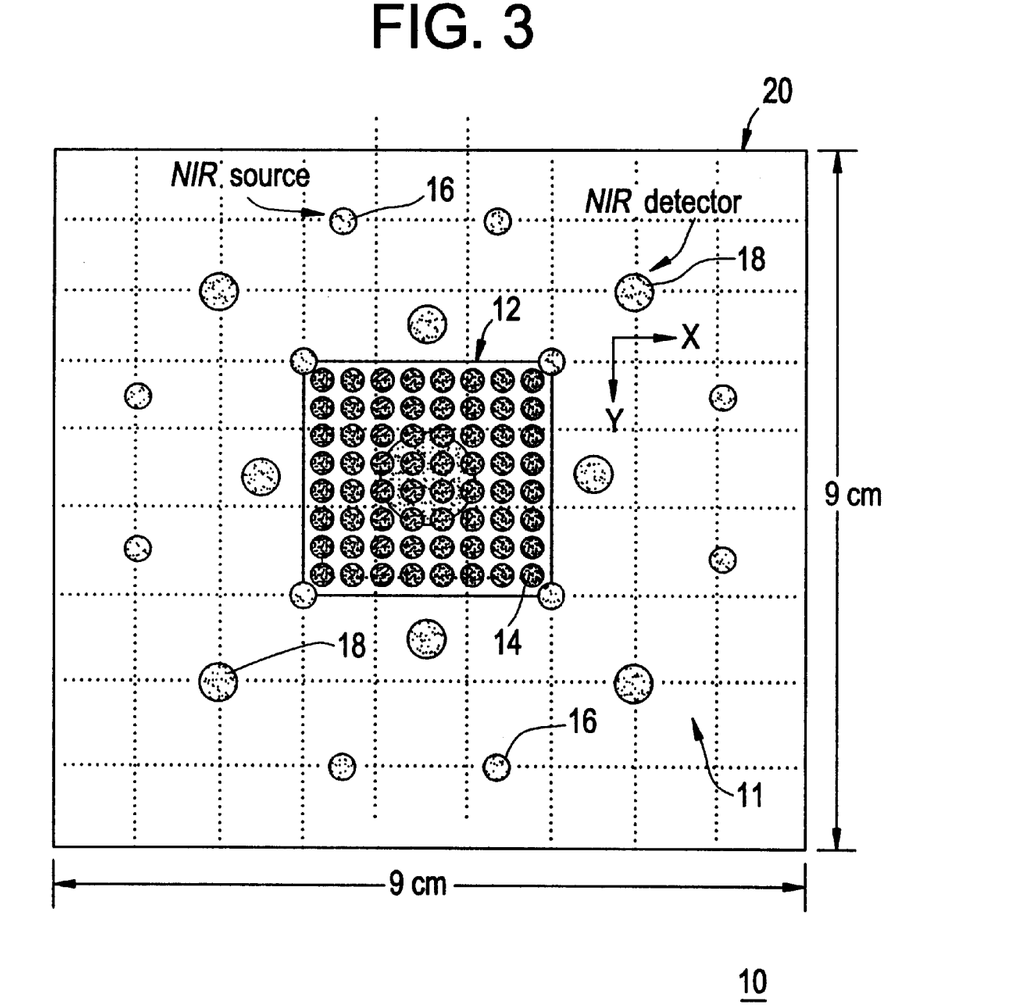
FIG. 3 is an alternative embodiment of the combined ultrasound and NIR light probe of the present invention.

FIG. 3 shows an alternative embodiment of the combined ultrasound and NIR light probe 10 of the present invention. In the embodiment shown in FIG. 3, a 2-D ultrasound array 12 together with an NIR optical array 11 of multiple laser sources 16 and optical detectors 18 are included in hand-held probe 10. The 2-D ultrasound array 12 occupies the center of the probe 10 and it consists of sixty-four, 1.5 mm diameter crystal transducer elements 14. The transducer elements 14 are deployed in a rectangular matrix with 4 mm spacing in both x and y directions. The center frequency of each transducer element 14 is 6 MHz and the bandwidth is 40%. The twelve sources 16 include optical fibers (source fibers) that extend through the probe support 20 at points around the periphery of the 2-D ultrasound array 12. The twelve source fibers are connected to twelve dual-wavelength optical laser diode sources (760 nm and 830 nm) (not shown). The eight optical detectors 18 include optical fibers (detector fibers) that extend through the probe support 20 at points around the periphery of the 2-D ultrasound array 12. The eight optical detector fibers are connected to eight Photo Multiplier (PMT) detectors. The ends of source and detector fibers are substantially flush with face surface 21. It will be recognized by one skilled in the art that sources 16 may include optical laser diode sources connected directly to probe 10, without the source fibers. Similarly, detectors 18 may include PMT detectors connected directly to the probe 10, without the detector fibers.

While FIGS. 1 and 3 show custom ultrasound 2-D arrays, it will be recognized, that any ultrasound 2-D array may be incorporated in the combined probe. For example, any commercially available ultrasound 2-D array can be used for combined probe 10. In addition, a one-dimensional (1-D), 1.5-dimensional (1.5-D), or 1.75 dimensional (1.75-D) ultrasound array can be used. A 1-D array can be mechanically rotated about the target area to obtain three-dimensional volumetric data and therefore spatial ultrasound images. It is further contemplated that the ultrasound array 12 can be releasably secured to the probe 10 to allow independent ultrasound or NIR imaging if needed.

Figure 4:
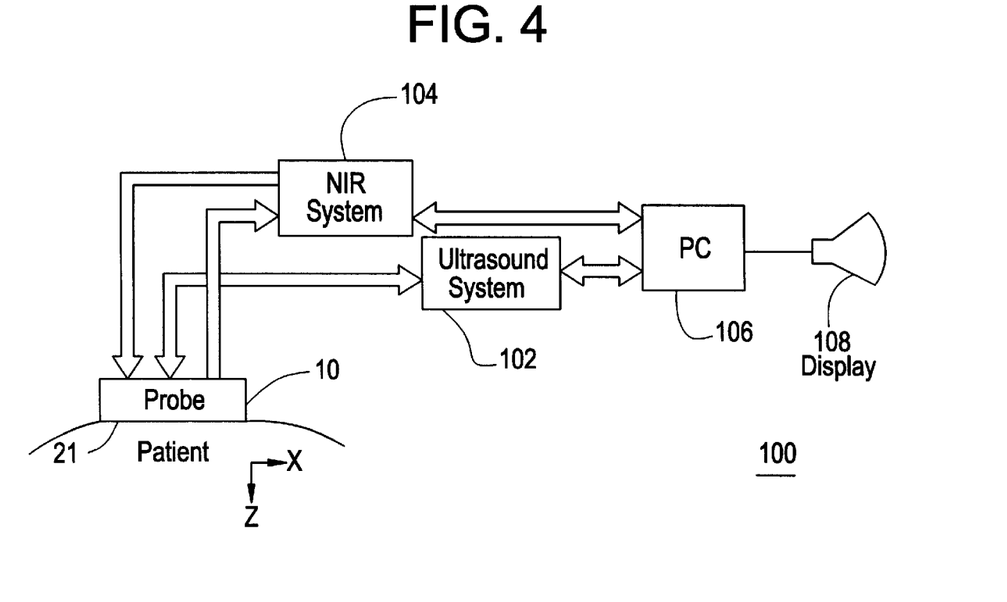
FIG. 4 is a simplified block diagram of a combined ultrasound and NIR light imaging system.

Referring now to FIG. 4, a simplified block diagram of a combined ultrasound and NIR light imaging system is shown generally at 100. The combined system 100 includes the combined ultrasound and NIR light probe 10, which is operatively connected to an ultrasound imaging system 102 and an NIR light imaging system 104. The ultrasound and NIR imaging systems 102, 104 provide output to an associated computer (PC) 106, which, in turn, provides output to a display device 108, such as a cathode ray tube (CRT) or a printer. The ultrasound and NIR imaging systems 102, 104 are described in further detail with reference to FIGS. 5 and 6. It will be recognized, however, that any ultrasound or NIR imaging system may be incorporated. For example, a commercially available ultrasound imaging system can be used for ultrasound imaging system 102. As another example, the NIR imaging system described by R. M. Danen, Y. Wang, X. D. Li, W. S. Thayer, and A. G. Yodh (1998), in their paper entitled "Regional Imager for Low Resolution Functional Imaging of the Brain with Diffusing Near-infrared Light," Photochemistry and Photobiology, January. 1998, vol 67, can be applied as NIR imaging system 104.

Figure 5:
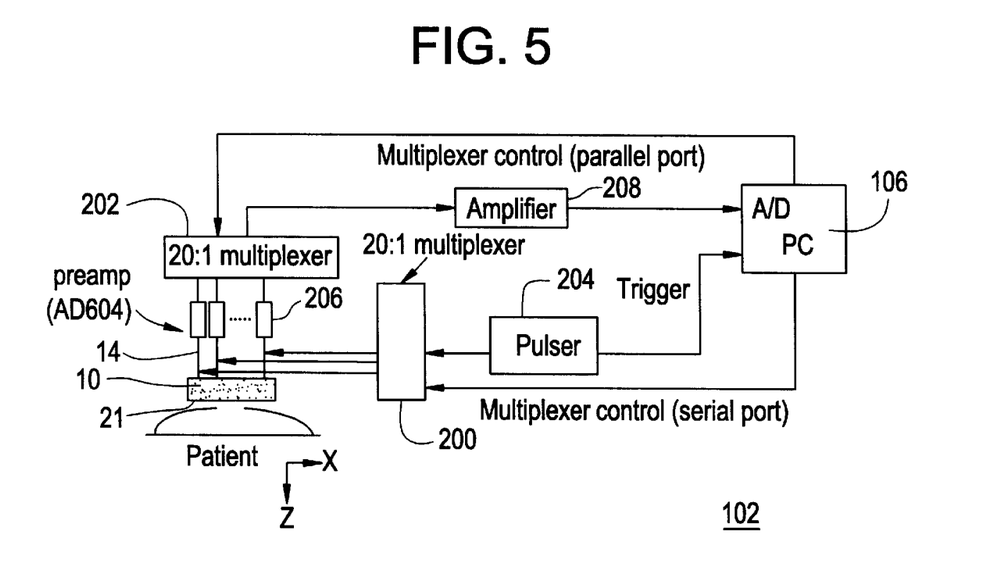
FIG. 5 is a simplified block diagram of the ultrasound imaging system of FIG. 4.

Referring to FIG. 5, the ultrasound imaging system 102 includes transmit and receive multiplexers (switches) 200 and 202, a pulser (transmitter) 204, and pre and post amplifiers 206 and 208. The PC 106 is programmed to perform various beamforming and signal processing algorithms. The transmit multiplexer 200 connects the pulser 204 with the elements 14 of the probe 10. The receive multiplexer 202 connects the post amplifier 208 with the elements 14 of the probe 10 via the pre amplifiers 206.

In general, a data acquisition cycle starts with a transmit period in which the pulser 204 excites one or more elements 14 with signals of various delays and amplitudes according to various transmit beamforming algorithms. After the transmit period, one or more elements 14 begin to receive the ultrasound echoes from various discontinuities in the medium (e.g. the patient) and to transform them into electrical signals. The received electrical signals are then amplified by pre amplifiers 206, multiplexed by multiplexer 202, and the resulting series of signals is amplified by post amplifier 208. The amplified series of signals is then provided to the PC 106, where the signals are processed in various ways, e.g. amplified, filtered, beamformed, detected, and eventually transformed into a set of digital values (pixels) that can be displayed on the display device 108 (FIG. 4).

More specifically, for the embodiment shown, data acquisition begins when the pulser 204 generates 1 cycle radio frequency (rf) pulse with a 120 volt peak that drives one element 14 at a time selected by the 20:1 high voltage multiplexer 200, such as that manufactured by the Matrix Corporation. The multiplexer 200 is controlled by the PC 106 through its serial port. The rf signals that return are received one at a time, amplified by the preamplifiers 206 (such as model number DDE 604, manufactured by Analog Devices, Inc.), and switched by a CMOS 20:1 multiplexer 202. The selected channel is amplified by the second stage amplifier 208 and sampled by a high-speed analog to digital conversion (A/D) board (such as that manufactured by Gage Applied, Inc.) within PC 106 at a sampling rate of 40 MHz. Measurements obtained from all transmission and reception positions are weighted to form the focused coherent beam output. The focal depth is approximately 30 mm. No beam steering is used in the image formation because of the sparse nature of the array. Therefore, the field of view is restricted to the area covered by the elements 12 (approximately 2 cm by 1.6 cm). A two dimensional x-y image slice is formed by detecting the envelope signals of coherent beams within a time window and summing the envelope signals within the window. A sequence of two dimensional x-y image slices is obtained by dividing the total propagation depth into consecutive time windows. The slice sickness varies from to 2 to 5 mm in depth.

Figure 6:
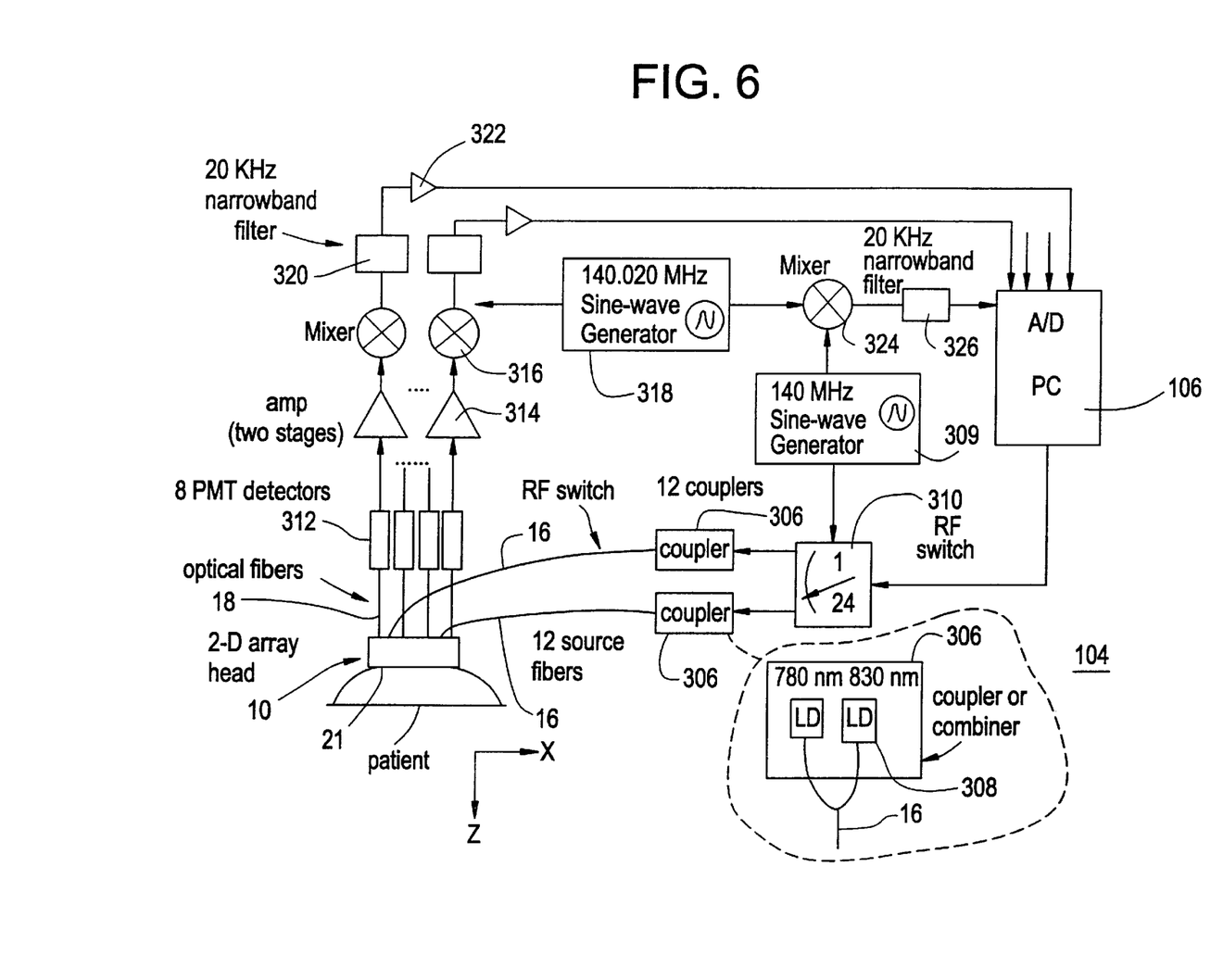
FIG. 6 is a simplified block diagram of the NIR light imaging system of FIG. 4.

Referring to FIG. 6, a block diagram of NIR imaging system 104 is shown. NIR imaging system 104 is shown here as configured for use with the probe 10 shown in FIG. 3; however, with modifications made for the number of laser diode sources 16 and light detectors 18, imaging system 104 can also be used with the probe 10 shown in FIG. 1.

On the source side of NIR imaging system 104, twelve optical couplers or combiners 306 each house dual wavelength (780 nm and 830 nm) laser diodes 308, as shown in the insert portion of FIG. 3. Optical couplers 306 include, for example, those manufactured by OZ optics, Inc. The output of laser diodes 308 are coupled to the transducer probe 10 through twelve, multi-mode optic fibers, to form NIR sources 16. Each laser diode 308 has its own driving circuit (not shown here) and its output intensity is modulated at 140.000 MHz by a local oscillator (sine wave generator) 309. The input of each laser diode 308 is coupled to a corresponding RF source switch 310. The twenty-four RF source switches 310 are controlled in series by the PC 106 to direct the output of the oscillator 309 to the laser diodes 308 corresponding to a single wavelength (780 nm or 830 nm). The laser diodes 308 corresponding to the selected wavelength then provide photon diffusion waves at the selected wavelength to the NIR source fibers, which project the photon diffusion waves into the medium (e.g. the patient).

On the reception side of NIR imaging system 104, light detectors 18 are formed from optical fibers that receive reflected photon diffusion waves from targets in the medium (e.g. the patient). The detector fibers guide the reflected waves to the input of a corresponding PMT detector 312. The parallel outputs of the eight PMT detectors 312 are amplified (40 dB) by amplifiers 314 and mixed with a 140.020 MHz output signal from a local oscillator 318 by mixers 316. The heterodyned signals at 20 kHz output by mixers 316 are filtered by 20 KHz narrowband filters 320 and further amplified (30B) by amplifiers 322. The amplified signals are then sampled by an analog to digital conversion (A/D) board, such as that manufactured by National Instruments, Inc., inside the PC 106. The sampling frequency of each channel is 250 KHz, which is well above the Nyquist sampling rate. The 140.000 and 140.020 MHz signals output by oscillators 309 and 318 respectively, are directly mixed by mixer 324 to produce 20 kHz reference signal. The 20 kHz reference signal is filtered by a 20 kHz narrow band filter 326, and provided as input to the PC 106.

PC 106 is programmed to perform a Hilbert transform on both sampled and reference waveforms. The amplitude of Hilbert transform of the sampled waveform corresponds to the measured amplitude, and the phase difference between the phases of Hilbert transforms of sampled and reference waveforms corresponds to the measured phase. Measurements made at the multiple source-detector positions can be used in various, well-known image reconstruction schemes to determine the absorption and scattering coefficients of the tissue volume at slice depths below the probe 10. In the present embodiment, PC 106 is programmed to apply a perturbation theory within the Rotov approximation to generate a set of coupled linear equations that relate the measured optical signals to the absorption and scattering variations in each volume element within the sample. PC 106 is programmed to perform an algebraic reconstruction technique to solve these equations iteratively. This reconstruction scheme yields an image of the optical properties of the three-dimensional volume (8.0cm by 6.4 cm by 54.0 cm) beneath the probe 10 surface. The reconstructed voxels measure 1.0cm by 1.0cm by 1.0cm, so the number of unknowns and the number of measured parameters are kept approximately the same; the images are virtually unchanged in reconstruction, with voxels of size 0.4cm by 0.4cm by 1.0cm. Therefore voxels of size 0.4cm by 0.4cm by 1.0cm are reconstructed for use with ultrasound images.

Figure 7:
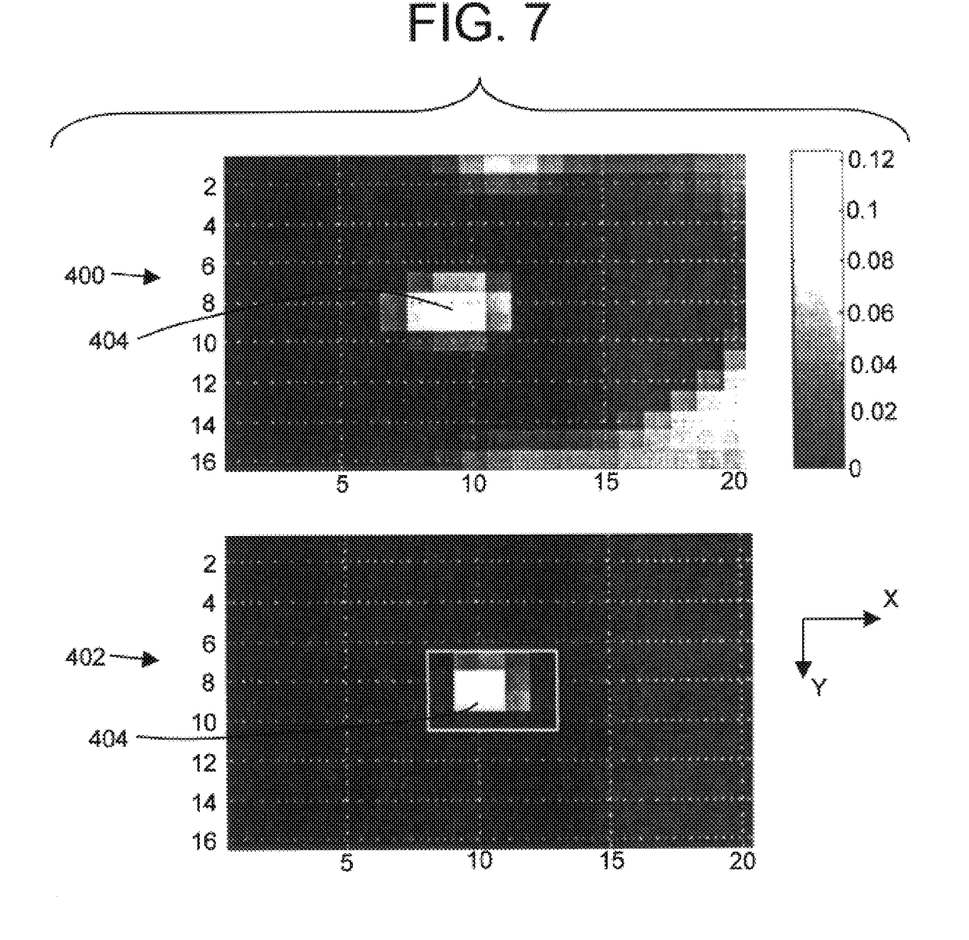
FIG. 7 is a view of optical absorption and ultrasound images of the same target, as provided by the combined ultrasound and NIR light imaging system of FIG. 4.

FIG. 7 shows an example of co-registered optical absorption and ultrasound images 400 and 402 of the same target 404 as obtained from the combined ultrasound and NIR light imaging system 100 and viewed on a screen or print-out of display device 108. The co-registered images 400 and 402 are positioned proximate each other on the screen or print-out so that the two images can be viewed simultaneously. The image pixel size is the same (4 mm by 4 mm) in both the ultrasound image 402 and the optical image 400. The shapes of the target 404 in both images 400 and 402 are similar, and locations of the target within the images 400 and 402 are approximately the same. The gray scale levels are the same in both images 400 and 402. In sum, the optical and ultrasound images 400 and 402 are co-registered on the same display. The combined ultrasound and NIR light imaging system 100 has been shown to achieve co-registration of optical and ultrasound images with an accuracy of about half a pixel size.

In the example shown in FIG. 7, the abscissa and ordinate are x and y spatial coordinates in the image plane (i.e. the x-y plane formed by probe 10). The optical image 400 is reconstructed at a given slice depth, for example 26 mm, in the z direction (i.e. normal to the probe 10 as shown in FIGS. 4–6). The ultrasound image 402 is obtained by summing up the envelopes of the beams in a range of approximately 1 mm less in depth than the given optical image slice depth to approximately 1mm greater in depth than the given optical image slice depth. For example, with an optical image slice depth of 26 mm, the ultrasound image 402 is obtained by summing the envelopes of the beams in a range from 25 mm to 27 mm in the z direction.

The combined ultrasound and NIR light imaging system 100, with the combined ultrasound and NIR light probe 10, provides co-registration of ultrasound and optical images. Co-registration of ultrasound and optical images provides a novel way to obtain the benefits of optical contrast and ultrasound imaging capabilities. Low-resolution, high-contrast optical images provide functional parameters such as oxygenation and blood volume which will add diagnostic information to the ultrasonically detected lesions. Furthermore, target structure information provided by ultrasound will help optical reconstruction algorithms to determine precisely optical properties. Therefore, the combined ultrasound and NIR light imaging system of the present invention increases the ability to distinguish a tumor from normal tissue.

While the invention has been described with reference to a preferred embodiment and various alternative embodiments, it will be understood by those skilled in the art that changes may be made and equivalents may be substituted for elements thereof without departing from the scope of invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A combined ultrasound and diffused light probe for use in imaging of a medium, the combined ultrasound and diffused light probe comprising:
    a plurality of ultrasound transducer elements configured to receive ultrasound echoes from the medium and transform the ultrasound echoes into electrical signals;
    a near-infrared light source positioned proximate to said plurality of ultrasound transducer elements, said near-infrared light source being configured to project photon diffusion waves into the medium; and
    a near-infrared light detector positioned proximate to said plurality of ultrasound transducer elements, said near-infrared light detector being configured to receive reflected photon diffusion waves from the medium.

2. The combined ultrasound and diffused light probe of claim 1, wherein said plurality of ultrasound transducer elements is formed in a two-dimensional array.

3. The combined ultrasound and diffused light probe of claim 1, wherein said plurality of ultrasound transducer elements is formed in array having dimensions selected from the group including one-dimensional, 1.5-dimensional, and 1.75-dimensional.

4. The combined ultrasound and diffused light probe of claim 1, wherein said plurality of ultrasound transducer elements is positioned between said nearinfrared light source and said near-infrared light detector.

5. The combined ultrasound and diffused light probe of claim 1, further comprising:
    a plurality of near-infrared light sources distributed around said plurality of ultrasound transducer elements; and
    a plurality of near-infrared light sensors distributed around said plurality of ultrasound transducer elements.

6. A combined ultrasound and diffused light imaging system for imaging a tissue volume, said combined ultrasound and diffused light imaging system comprising:
    a probe including
        a plurality of ultrasound transducer elements configured to receive ultrasound echoes from the tissue volume and to transform the ultrasound echoes into electrical signals,
        a near-infrared light source positioned proximate to said plurality of ultrasound transducer elements, said near-infrared light source being configured to project photon diffusion waves into the tissue volume, and
        a near-infrared light detector positioned proximate to said plurality of ultrasound transducer elements, said near-infrared light detector being configured to receive reflected photon diffusion waves from the tissue volume;
    a near-infrared light imaging system configured to receive said reflected photon diffusion waves from said near-infrared light detector and provide a first image of the tissue volume; and
    an ultrasound imaging system configured to receive said electrical signals and provide a second image of the tissue volume.

7. The combined ultrasound and diffused light imaging system of claim 6, wherein said plurality of ultrasound transducer elements is formed in a two-dimensional array.

8. The combined ultrasound and diffused light imaging system of claim 6, wherein said plurality of ultrasound transducer elements is formed in array having dimensions selected from the group including one-dimensional, 1.5-dimensional, and 1.75-dimensional.

9. The combined ultrasound and diffused light imaging system of claim 6, wherein said plurality of ultrasound transducer elements is positioned between said near-infrared light source and said near-infrared light detector.

10. The combined ultrasound and diffused light imaging system of claim 6, wherein said probe further includes:
    a plurality of near-infrared light sources distributed around said plurality of ultrasound transducer elements; and
    a plurality of near-infrared light detectors distributed around said plurality of ultrasound transducer elements.

11. The combined ultrasound and diffused light imaging system of claim 6, wherein said first and second images are provided on a single display.

12. The combined ultrasound and diffused light imaging system of claim 6, wherein said first and second images have the same scale.

13. The combined ultrasound and diffused light imaging system of claim 6, wherein said first and second images have the same grayscale and/or color scheme.

14. The combined ultrasound and diffused light imaging system of claim 6, wherein the said first and second images each include an image of a target within the tissue volume, the image of the target being positioned in the same location in said first and second images.

15. A combined ultrasound and diffused light imaging system for imaging a tissue volume, said combined ultrasound and diffused light imaging system comprising:
    a near-infrared light imaging system configured to provide a first image of the tissue volume; and
    an ultrasound imaging system configured provide a second image of the tissue volume, wherein said first and second images are provided on a single display.

16. The combined ultrasound and diffused light imaging system of claim 15, wherein said first and second images have the same scale.

17. The combined ultrasound and diffused light imaging system of claim 15, wherein said first and second images have the same grayscale and/or color scheme.

18. The combined ultrasound and diffused light imaging system of claim 15, wherein the said first and second images each include an image of a target within the tissue volume, the image of the target being positioned in the same location in said first and second images.

* * * * *

UNITED STATES PATENT AND TRADEMARK OFFICE
CERTIFICATE OF CORRECTION

PATENT NO.   : 6,264,610 B1
DATED        : July 24, 2001
INVENTOR(S)  : Quing Zhu

It is certified that error appears in the above-identified patent and that said Letters Patent is hereby corrected as shown below:

Column 4,
Line 50, after "Photobiology," delete "January." and insert therefor -- January --

Column 6,
Line 3, after "amplified" (first occurrence) delete "(30B)" and insert therefor
-- (30dB) --
Line 31, after "volume" delete "(8.0cm" and insert therefor -- (8.0 cm --
Line 33, after "measure" delete "1.0cm by 1.0cm by 1.0cm" and insert therefor
-- 1.0 cm by 1.0 cm by 1.0 cm --
Line 36, after "of size" delete "0.4cm by 0.4cm by 1.0cm" and insert therefor
-- 0.4 cm by 0.4 cm by 1.0 cm --
Line 37, after "of size" delete "0.4cm by 0.4cm by 1.0cm" and insert therefor
-- 0.4 cm by 0.4 cm by 1.0 cm --

Signed and Sealed this

Fifteenth Day of March, 2005

JON W. DUDAS
*Director of the United States Patent and Trademark Office*